United States Patent
Otani et al.

(10) Patent No.: US 9,312,100 B2
(45) Date of Patent: *Apr. 12, 2016

(54) SENSITIVITY CORRECTION METHOD FOR DOSE MONITORING DEVICE AND PARTICLE BEAM THERAPY SYSTEM

(71) Applicant: MITSUBISHI ELECTRIC CORPORATION, Chiyoda-ku (JP)

(72) Inventors: Toshihiro Otani, Tokyo (JP); Hisashi Harada, Tokyo (JP); Masahiro Ikeda, Tokyo (JP); Kazushi Hanakawa, Tokyo (JP); Taizo Honda, Tokyo (JP)

(73) Assignee: MITSUBISHI ELECTRIC CORPORATION, Chiyoda-Ku, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/478,143

(22) Filed: Sep. 5, 2014

(65) Prior Publication Data

US 2014/0374624 A1 Dec. 25, 2014

Related U.S. Application Data

(63) Continuation of application No. 13/262,866, filed as application No. PCT/JP2011/055638 on Mar. 10, 2011, now Pat. No. 8,854,048.

(51) Int. Cl.
*G01N 27/62* (2006.01)
*H01J 37/304* (2006.01)
(Continued)

(52) U.S. Cl.
CPC ............. *H01J 37/304* (2013.01); *A61N 5/1048* (2013.01); *A61N 5/1071* (2013.01); *A61N 5/1077* (2013.01); *H01J 47/02* (2013.01); *A61N 2005/1087* (2013.01)

(58) Field of Classification Search
CPC . A61N 5/1031; A61N 5/1039; A61N 5/1048; A61N 5/10; A61N 5/1071; A61N 5/1077; A61N 5/1075; A61N 5/1043; A61N 2005/1087; A61N 2005/1074; G01N 27/62; H01J 37/304; H01J 37/3171; H01J 3/26

USPC ............... 324/464, 467, 463, 71.3, 71.4, 214; 250/492.1, 492.2, 492.3, 396 R, 393, 250/397, 306

See application file for complete search history.

(56) References Cited

U.S. PATENT DOCUMENTS 6,218,675 B1 * 4/2001 Akiyama ............. A61N 5/1043
                                               250/396 ML
6,717,162 B1    4/2004 Jongen
                        (Continued)

FOREIGN PATENT DOCUMENTS

JP    1-098985 A    4/1989
JP    1-210890 A    8/1989
                        (Continued)

OTHER PUBLICATIONS

International Search Report (PCT/ISA/210) issued on May 24, 2011, by Japanese Patent Office as the International Searching Authority for International Application No. PCT/JP2011/055638, 3 pages (with English language translation of category of cited documents).

(Continued)

Primary Examiner — Tung X Nguyen
Assistant Examiner — Thang Le
(74) *Attorney, Agent, or Firm* — Buchanan Ingersoll & Rooney PC (57) ABSTRACT

In a particle beam therapy system which scans a particle beam and irradiates the particle beam to an irradiation position of an irradiation subject and has a dose monitoring device for measuring a dose of the particle beam and an ionization chamber smaller than the dose monitoring device, the ionization chamber measuring a dose of a particle beam passing through the dose monitoring device, the dose of the particle beam irradiated by the dose monitoring device is measured; the dose of the particle beam passing through the dose monitoring device is measured by the small ionization chamber; and a correction coefficient of the dose measured by the dose monitoring device corresponding to the irradiation position is found based on the dose of the particle beam measured by the small ionization chamber.

18 Claims, 8 Drawing Sheets

(51) Int. Cl.
*A61N 5/10* (2006.01)
*H01J 47/02* (2006.01)

(56) References Cited

U.S. PATENT DOCUMENTS

| | | | |
|---|---|---|---|
| 6,736,831 B1 | 5/2004 | Hartmann et al. | |
| 7,049,613 B2 * | 5/2006 | Yanagisawa | G21K 1/10 250/492.3 |
| 7,122,811 B2 * | 10/2006 | Matsuda | A61N 5/10 250/492.3 |
| 7,323,700 B1 | 1/2008 | Ledoux et al. | |
| 7,579,608 B2 * | 8/2009 | Takahashi | A61N 5/1042 250/492.3 |
| 7,692,168 B2 | 4/2010 | Moriyama et al. | |
| 7,825,388 B2 | 11/2010 | Nihongi et al. | |
| 8,563,943 B2 * | 10/2013 | Iwata et al. | 250/397 |
| 2004/0056210 A1 | 3/2004 | Scherer | |
| 2005/0247890 A1 | 11/2005 | Norimine et al. | |
| 2007/0114473 A1 | 5/2007 | Matsuda et al. | |
| 2007/0252093 A1 | 11/2007 | Fujimaki et al. | |
| 2011/0121195 A1 | 5/2011 | Harada et al. | |
| 2011/0174994 A1 | 7/2011 | Iwata | |
| 2011/0260074 A1 | 10/2011 | Honda et al. | |
| 2012/0029862 A1 | 2/2012 | Scholz et al. | |
| 2012/0305796 A1 | 12/2012 | Iseki et al. | |

FOREIGN PATENT DOCUMENTS

| | | |
|---|---|---|
| JP | 2003-294848 A | 10/2003 |
| JP | 2010-054309 A | 3/2010 |
| JP | 2010-082229 A | 4/2010 |
| JP | 4580465 B2 | 11/2010 |
| WO | WO 2009/139043 A1 | 11/2009 |

OTHER PUBLICATIONS

Written Opinion (PCT/ISA/237) issued on May 24, 2011, by Japanese Patent Office as the International Searching Authority for International Application No. PCT/JP2011/055638, 4 pages (with partial English language translation).

Taiwanese Office Action dated Oct. 9, 2013, issued in corresponding Taiwanese Application No. 100137488, and a Partial English Translation of the Taiwanese Office Action, (33 pgs).

\* cited by examiner

SENSITIVITY CORRECTION METHOD FOR DOSE MONITORING DEVICE AND PARTICLE BEAM THERAPY SYSTEM

TECHNICAL FIELD

The present invention relates to particle beam therapy systems which perform scanning irradiation and, more particularly, relates to a sensitivity correction method for a dose monitoring device of a particle beam for use in an irradiation apparatus of its system and a particle beam therapy system.

BACKGROUND ART

A dose monitoring device is known as so-called an ionization chamber. For example, in Patent Document 1, there is disclosed a monitoring device for measuring a particle beam in which a collector electrode which is formed by adhering metal to a resin plate by vapor deposition or plating and a high voltage electrode are arranged in face-to-face relation by making insulation plates intervene in order to improve strain of the collector electrode.

In Patent Document 2, there is disclosed a radiation dose monitor in which a high voltage electrode and a collector electrode are supported by insulation support bodies disposed with an interval in order to prevent ionization current from changing due to deflection.

Further, in Patent Document 3, there is disclosed a transmission type dosimeter in which a dose of radiation passing through the dosimeter is measured and the measured dose is corrected on the basis of the amount of deformation of a container of the dosimeter due to atmospheric pressure.

RELATED ART DOCUMENT

Patent Document

Patent Document 1: Japanese Unexamined Patent Publication No. H1-98985
Patent Document 2: Japanese Unexamined Patent Publication No. H1-210890
Patent Document 3: Japanese Unexamined Patent Publication No. 2010-54309

DISCLOSURE OF THE INVENTION

Problems to be Solved by the Invention

However, in the conventional dose monitoring device (dose monitor), solution for countermeasures in the case of the occurrence of deflection that is inevitable for the collector electrode are not implemented. In the dose monitoring device, the deflection of the collector electrode is small and the influence due to the deflection can be negligible in the case where a transmission window of a particle beam is small in bore diameter; however, with an increase in the bore diameter, the influence due to the deflection of the collector electrode cannot be negligible and it causes a problem that deteriorates measurement accuracy of the dose.

In view of the aforementioned problem, the present invention is to provide a sensitivity correction method for a dose monitoring device and a particle beam therapy system, in each of which a correction coefficient of a dose measured by a dose monitoring device corresponding to an irradiation position of an irradiation subject is found and sensitivity of the dose monitoring device is corrected against deterioration in measurement accuracy of the dose due to deflection of an electrode.

Means for Solving the Problems

According to the present invention, there is provided a sensitivity correction method for a dose monitoring device in a particle beam therapy system which scans a particle beam and irradiates the particle beam to an irradiation position of an irradiation subject, the particle beam therapy system including: a dose monitoring device which measures a dose of the particle beam; and an ionization chamber smaller than the dose monitoring device, the ionization chamber measuring a dose of a particle beam passing through the dose monitoring device. The sensitivity correction method includes the steps of: measuring the dose of the particle beam irradiated by the dose monitoring device; measuring the dose of the particle beam passing through the dose monitoring device by the small ionization chamber; and finding a correction coefficient of the dose measured by the dose monitoring device corresponding to the irradiation position based on the dose of the particle beam measured by the small ionization chamber.

According to the present invention, there is provided a particle beam therapy system which scans a particle beam and irradiates the particle beam to an irradiation position of an irradiation subject, the particle beam therapy system including: a dose monitoring device which measures a dose of the particle beam; an ionization chamber smaller than the dose monitoring device, the ionization chamber measuring a dose of a particle beam passing through the dose monitoring device; and a calculation unit which finds a correction coefficient of the dose measured by the dose monitoring device corresponding to the irradiation position based on the dose of the particle beam measured by the small ionization chamber, from the dose of the irradiated particle beam measured by the dose monitoring device, the irradiation position, and the dose of the particle beam passing through the dose monitoring device measured by the small ionization chamber. The irradiation dose is adjusted based on the correction coefficient.

Advantageous Effect of the Invention

According to the sensitivity correction method for the dose monitoring device and the particle beam therapy system of the present invention, the correction coefficient of the dose measured by the dose monitoring device corresponding to the irradiation position of an irradiation subject is found and sensitivity of the dose monitoring device is corrected against deterioration in measurement accuracy of the dose due to deflection of an electrode; whereby, the dose monitoring device can perform highly accurate dose measurement in an irradiation position of an irradiation subject even in a relatively large irradiation field necessary for scanning irradiation.

Objects, features, aspects, and advantageous effects other than the foregoing of the present invention will become more apparent from the following detailed description of the present invention for referring to the accompanying drawings.

MODE FOR CARRYING OUT THE INVENTION

Embodiment 1

Figure 1:
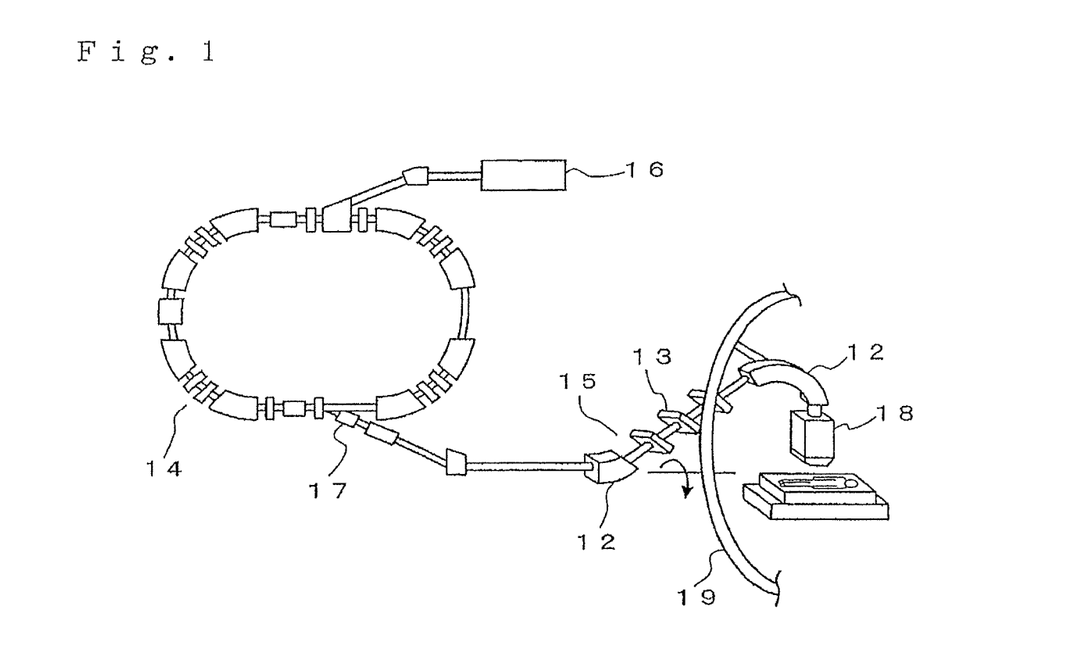
FIG. 1 is a schematic whole configuration view showing a particle beam therapy system in which a dose monitoring device according to Embodiment 1 of the present invention is located.
Figure 2:
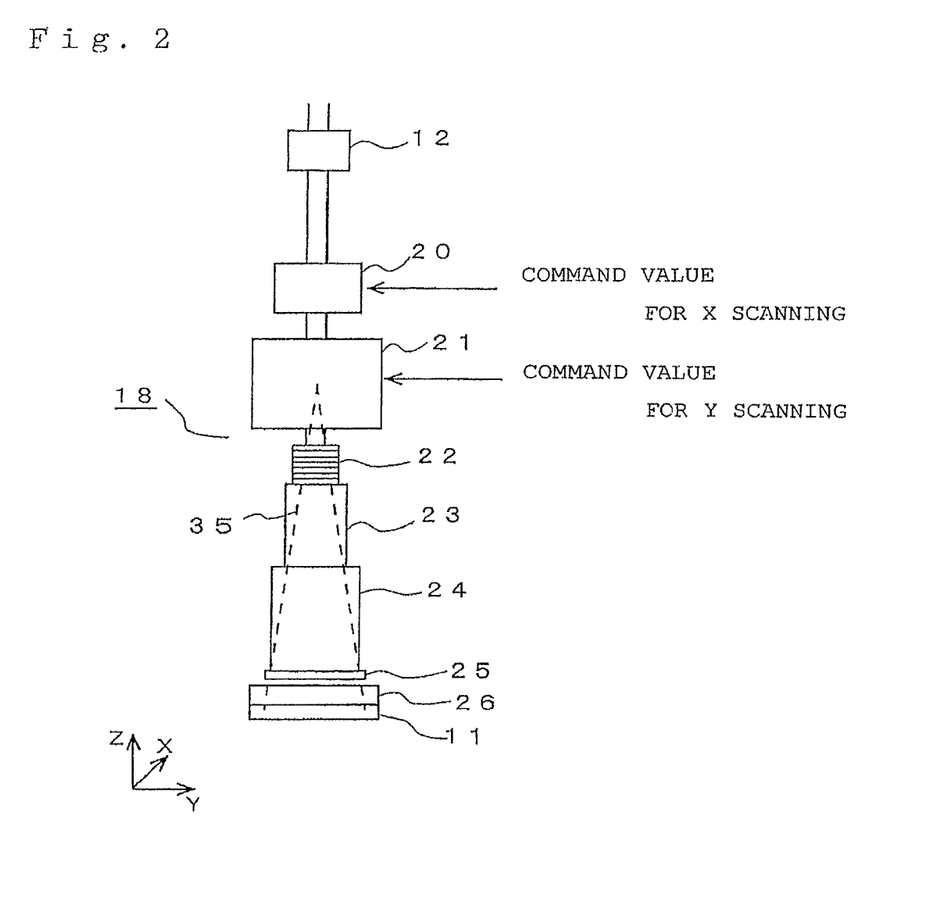
FIG. 2 is a configuration view showing an irradiation apparatus of the particle beam therapy system in which the dose monitoring device according to Embodiment 1 is located.

FIG. 1 is a schematic whole configuration view showing a particle beam therapy system in which a dose monitoring device according to Embodiment 1 of the present invention is located. FIG. 2 is a configuration view showing an irradiation apparatus of the particle beam therapy system in which the dose monitoring device according to Embodiment 1 is located. In FIG. 1, a charged particle baam (particle beam) generated by an injector 16 and accelerated at a former stage is made incident to an accelerator (synchrotron) 14 and is accelerated to necessary beam energy. The particle beam accelerated to necessary beam energy is emitted from an outgoing deflector 17 to a beam transport apparatus 15 and then reaches an irradiation apparatus 18 to be irradiated to an irradiation position of an irradiation subject. The beam transport apparatus 15 has a focusing electromagnet 13 and a bending electromagnet 12. A part of the beam transport apparatus 15 and the irradiation apparatus 18 are mounted on a rotating gantry 19, and an irradiation direction of the irradiation apparatus 18 can be changed by the rotation of the rotating gantry 19 (shown by an arrow in the drawing).

FIG. 2 is an enlarged configuration view of the irradiation apparatus 18 and a charged particle beam is introduced to the irradiation apparatus 18 via the bending electromagnet 12 of the beam transport apparatus 15. The charged particle beam is scanned by an X direction scanning electromagnet 20 to be controlled by a command value for X direction scanning (the amount of excitation) and a Y direction scanning electromagnet 21 to be controlled by a command value for Y direction scanning (the amount of excitation). The scanned charged particle beam is emitted from a beam taking-out window 25 which takes out the beam via a duct expansion and contraction unit (bellows) 22 for expanding and contracting ducts and vacuum ducts 23,24. FIG. 2 shows conditions in which particle a beam 35 is scanned in a Y axial direction. Arrows XYZ show XYZ axial directions.

The particle beam therapy system which achieves scanning irradiation is different from normal irradiation and layer-stack irradiation in that a dose is controlled with respect to a spot irradiated on an XY flat surface and therefore a dose monitoring device 26 of a particle beam and a position monitor 11 which measures a position of the particle beam are arranged in a lower stream of the beam taking-out window 25. The dose monitoring device 26 and the position monitor 11 are arranged at a right angle to an axis of a traveling direction of the particle beam. Incidentally, the same reference numerals as those shown in respective drawings represent the same or corresponding elements.

Figure 3:
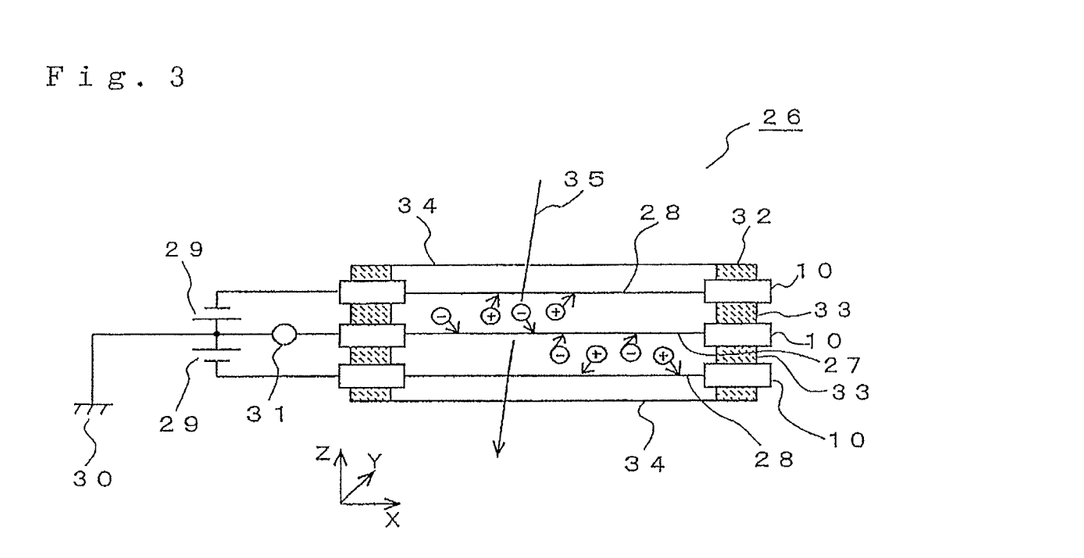
FIG. 3 is a configuration view showing the dose monitoring device according to Embodiment 1 along with a view for explaining its operation.

FIG. 3 is a configuration view showing the dose monitoring device (ionization chamber) according to Embodiment 1 along with a view for explaining its operation. The dose monitoring device 26 has a collector electrode 27 and a high voltage electrode 28, each of which is retained by electrode supports 10. The collector electrode 27 and the high voltage electrode 28 are made of metal sheet, such as aluminum. A power source 29 is connected between the collector electrode 27 and the high voltage electrode 28. The collector electrode 27 is, for example, 0 V; and the high voltage electrode 28 is, for example, −1 kV or −3 kV. An ammeter 31 is connected between the collector electrode 27 and the power source 29. The dose monitoring device 26 is covered by a container 32 and an insulator 33 intervenes between the collector electrode 27 and the high voltage electrode 28 to provide and electrical insulation and mechanical support. The dose monitoring device 26 is, for example, an open-air ionization chamber and has a transmission window 34 of the particle beam on each of both surfaces of parallel flat plate shape.

In FIG. 3, when the particle beam 35 passes through in the dose monitoring device 26 filled with a gaseous substance (for example, air), the particle beam 35 impinges on molecules of the gaseous substance and the gaseous substance is ionized. When an electric field is applied between the collector electrode 27 and the high voltage electrode 28 using the high voltage power source 29, an ionized electron $e^-$ is collected on the collector electrode 27 and an ion $i^+$ is collected on the high voltage electrode 28. The number of the electrons $e^-$ and ions $i^+$ to be ionized is proportional to the strength of the particle beam passing through. The strength of the particle beam is measured by a current measured by the ammeter 31.

By the way, in the particle beam therapy system which achieves the scanning irradiation, the spot size of the particle beam preferably reduces an increase due to scattering. Therefore, in order to reduce the influence of the scattering in the dose monitoring device 26, the dose monitoring device 26 is located at a position near the lowermost stream of the irradiation apparatus 18 in FIG. 2. The position is near the lowermost stream and therefore an irradiation field of the particle beam of the irradiation apparatus 18 increases. In order to measure the particle beam of the large irradiation field, the dose monitoring device 26 increases in measurement effective area. If the measurement effective area increases, the collector electrode 27 is not completely parallel to the high voltage electrode 28 in the whole region; and accordingly, nonnegligible deflection is generated in the measurement of the strength of the particle beam.

Figure 4:
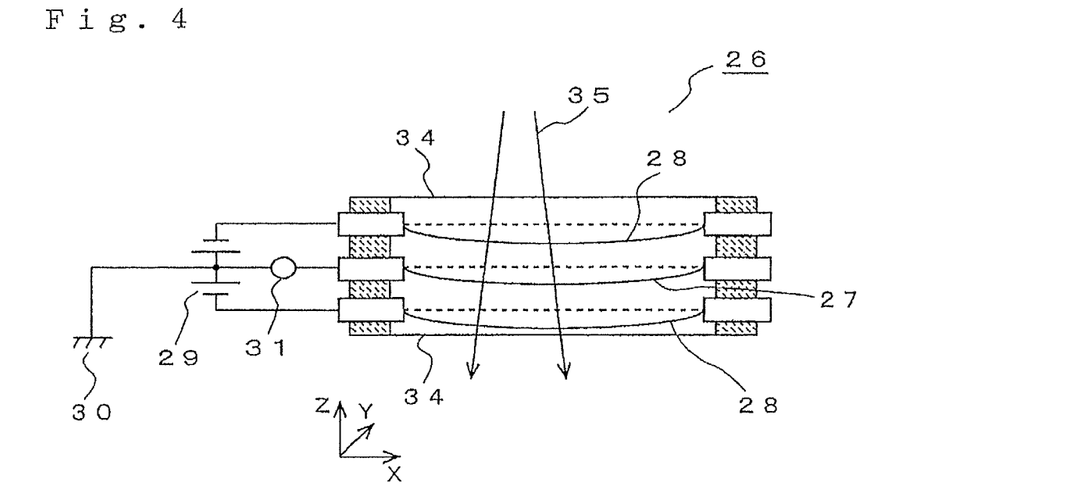
FIG. 4 is a view for explaining deflection of electrodes of the dose monitoring device and deterioration in measurement of the strength of a particle beam.

FIG. 4 is a view for explaining deflection of the electrodes of the dose monitoring device 26 and deterioration in measurement of the strength of the particle beam. The collector electrode 27 and the high voltage electrode 28 generate deflection by electromagnetic pressure between both electrodes and gravity. Dashed lines show a parallel state where deflection is not present in both electrodes 27,28. The electrodes 27,28 deflect; and accordingly, variation is generated in the distance between both electrodes 27,28 at a position (position on an XY flat surface) in the measurement effective area of both electrodes 27,28, for example, at the center and a peripheral portion in addition to an irradiation angle of the particle beam, and the variation is assumed to be generated in the amount of gaseous substances between both electrodes 27,28. Therefore, measured values are different at an irradiation position within the measurement effective area with respect to the same strength of the particle beam and thus measurement accuracy of the strength of the particle beam deteriorates.

Figure 5:
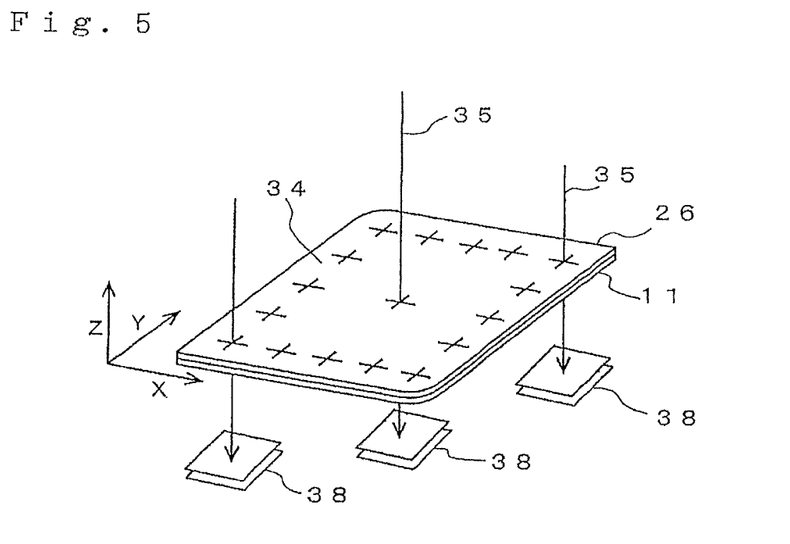
FIG. 5 is a view for explaining a sensitivity correction method for the dose monitoring device in Embodiment 1.

FIG. 5 is a view for explaining a sensitivity correction method for the dose monitoring device in Embodiment 1. The flat surface (XY surface) of the dose monitoring device 26 is formed with the transmission window 34 of the particle beam in its central portion and is disposed in perpendicular to the axis (Z axis) of the traveling direction of the particle beam. The position monitor 11 is disposed closely to the lower stream of the dose monitoring device 26, and its flat surface (XY surface) is disposed in perpendicular to the axis (Z axis) of the traveling direction of the particle beam. Incidentally, the location of the position monitor 11 may be permissible if the location is a position where an irradiation position of an irradiation subject can be measured (converted and measured), and the position monitor 11 may be disposed on the upper stream side of the dose monitoring device 26 or may be separately disposed from the dose monitoring device 26.

A small parallel flat plate type ionization chamber 38 is disposed in a lower stream of the dose monitoring device 26 and the position monitor 11. The small parallel flat plate type ionization chamber 38 is suitable for measurement in which a transmission window of a particle beam is small in bore diameter and is narrow range; and the deflection of the electrodes can be negligible and highly accurate measurement can be performed with respect to the strength of the particle beam. For example, the Bragg Peak Chamber (trade name), which is commercially available as one type of IONIZING RADIAION by PTW, is suitable as the small parallel flat plate type ionization chamber 38; a flat plate surface provided with a transmission window of a particle beam is, for example, approximately a diameter of 80 mm which is sufficiently larger as compared to, for example, a beam size of $1\sigma=5$ mm; and most particles can be made pass through the flat plate surface. The configuration of the Bragg Peak Chamber is such that the dose monitoring device 26 (the transmission window in the XY flat surface, that is, the irradiation field is, for example, a size of 400 mm×300 mm) is reduced in size and the configuration is similar thereto. The small parallel flat plate type ionization chamber 38 is disposed at an irradiation position of the particle beam during sensitivity correction of the dose monitoring device 26; its position may be changed on a predetermined XY flat surface (flat surface perpendicular to the Z axis of the traveling direction of the particle beam) during the sensitivity correction; and the small parallel flat plate type ionization chamber 38 is removed after the sensitivity correction.

The sensitivity correction method for the dose monitoring device 26 is performed as follows. For example, on the basis of an irradiation position to be set based on energy of a particle beam and the amount of excitation of X,Y direction scanning electromagnets commanded by using an irradiation position setting apparatus in which a treatment planning system has, the particle beam is scanned and the particle beam is irradiated to the irradiation position of an irradiation subject. In the arrangement shown in FIG. 5, first, the particle beam 35 is irradiated on the axis (Z axis) of the traveling direction. The particle beam 35 passes through the original point (x=0, y=0) on the XY flat surface of the dose monitoring device 26 and the original point (x=0, y=0) on the XY flat surface of the position monitor 11; and then, the particle beam 35 reaches the small parallel flat plate type ionization chamber 38 disposed at the original point (x=0, y=0) on the XY flat surface of the irradiation position of the irradiation subject. At this time, as far as the dose monitoring device 26 is concerned, current corresponding to the strength of the particle beam is obtained by the ammeter 31 and the current is converted to a count value $D_{0,0}$ corresponding to the irradiation position of the irradiation subject. As far as the position monitor 11 is concerned, the irradiation position (0,0) on the XY flat surface of the irradiation position of the irradiation subject is measured (converted and measured). As far as the small parallel flat plate type ionization chamber 38 is concerned, current corresponding to the strength of the particle beam is obtained by an ammeter (not shown in the drawing) and the current is converted to electric charge $C_{0,0}$ of the small parallel flat plate type ionization chamber 38 corresponding to the irradiation position [irradiation position (0,0)] of the irradiation subject. In this case, the ionization chamber changes in sensitivity due to a mass of gas which is present between the electrodes; and therefore, sensitivity correction needs to be performed in response to internal pressure and temperature. However, both of the dose monitoring device 26 and the small parallel flat plate type ionization chamber 38 use an open-air type; and accordingly, the influences of the temperature and atmospheric pressure are balanced out and thus the correction does not need to be performed and it becomes possible to calculate from only the obtained amount of electric charge.

The strength of the particle beam (electric charge) measured by the small parallel flat plate type ionization chamber 38 is highly accurate; and therefore, the measured value is set as a standard and a calibration coefficient (correction coefficient) $a_{0,0}$ corresponding to the irradiation position (0,0) of the dose monitoring device 26 is calculated using Formula (1).

$$C_{x,y} = a_{x,y} \cdot D_{x,y} \quad (1)$$

where, $D_{x,y}$: a count value of a dose monitoring device corresponding to an irradiation position (x,y) of an irradiation subject;

$a_{x,y}$: a calibration coefficient of the dose monitoring device corresponding to the irradiation position (x,y) of the irradiation subject; and $C_{x,y}$: an electric charge of the small parallel flat plate type ionization chamber corresponding to the irradiation position (x,y) of the irradiation subject.

Incidentally, the irradiation position (x,y) of the irradiation subject shows a position on the XY flat surface of the irradiation position.

$$a_{0,0} = C_{0,0}/D_{0,0} \quad (2)$$

Next, the irradiation position of the irradiation subject is changed, the irradiation position of the particle beam on the XY flat surface of the dose monitoring device 26 is changed, and the small parallel flat plate type ionization chamber 38 is also changed to a position where the particle beam is irradiated on a predetermined XY flat surface. In this case, the irradiation position (x,y) on the XY flat surface of the irradiation position of the irradiation subject is measured (converted and measured) by the position monitor 11. The count value $D_{x,y}$ is measured by the dose monitoring device 26 and the electric charge $C_{x,y}$ is measured by the small parallel flat plate type ionization chamber 38. These measured values are substituted for Formula (1), and the calibration coefficient (correction coefficient) $a_{x,y}$ at this time is obtained by Formula (3).

$$a_{x,y} = C_{x,y}/D_{x,y} \quad (3)$$

Further, the irradiation position of the irradiation subject is changed, the irradiation position of the particle beam on the XY flat surface of the dose monitoring device 26 is changed to other position, and the small parallel flat plate type ionization chamber 38 is also changed to other position where the particle beam is irradiated on a predetermined XY flat surface; and accordingly, the calibration coefficient ax,y at other irradiation position of the dose monitoring device 26 can be obtained by Formula (3) in a similar way.

In this way, the calibration coefficient (correction coefficient) of the dose measured by the dose monitoring device corresponding to the irradiation position of the irradiation subject can be found based on the dose of the particle beam measured by the small parallel flat plate type ionization chamber 38.

Furthermore, when the calibration coefficient ao,o at the position (0,0) of the irradiation position of the irradiation subject is set as a standard, a correction coefficient Ax,y at other irradiation position (x,y) of the irradiation subject can be found by Formula (4) as a ratio with respect to a reference position (0,0).

$$Ax,y=ax,y/ao,o \qquad (4)$$

In this way, the calibration coefficient (correction coefficient) of the dose monitoring device in the case where the irradiation position of the irradiation subject of the particle beam is on the axis of the traveling direction of the particle beam is set as a standard, and a correction coefficient of the dose monitoring device in the case where the irradiation position of the irradiation subject of the particle beam is different from the axis of the traveling direction of the particle beam may be found by a ratio with the calibration coefficient set as the standard.

Figure 7:
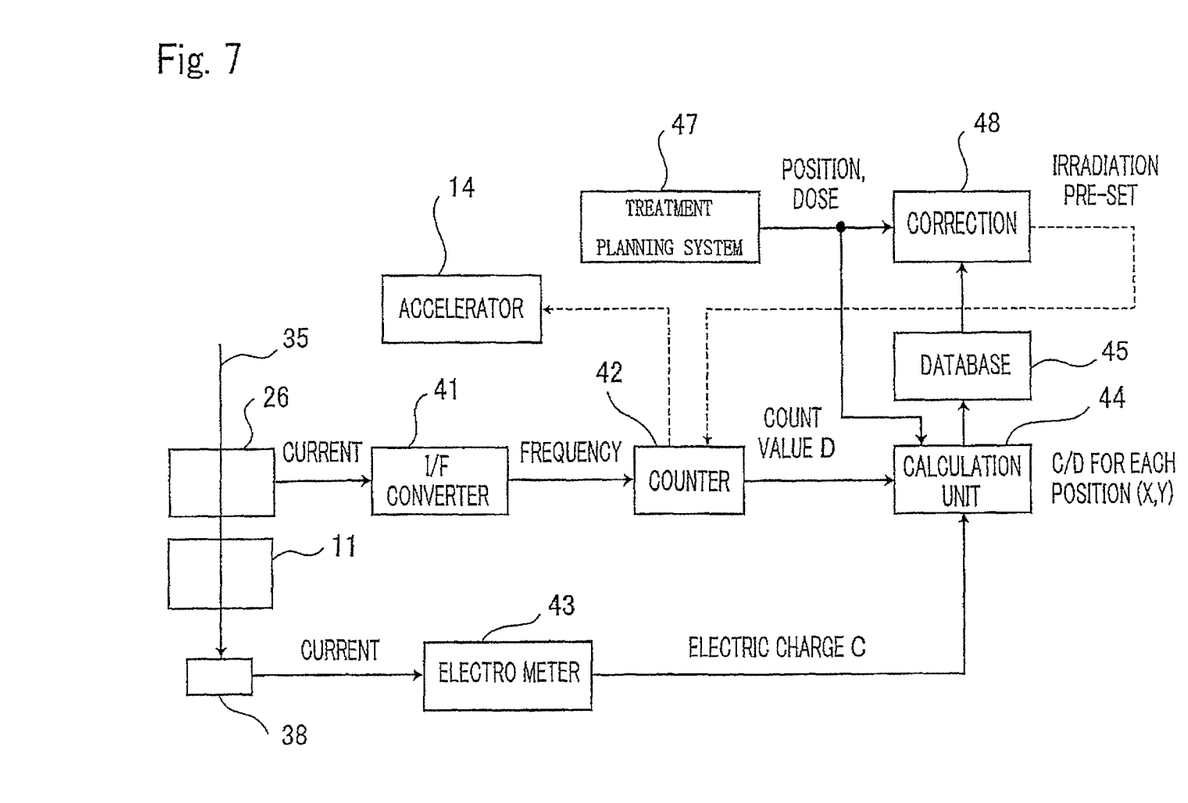
FIG. 7 is a block diagram showing a particle beam therapy system using a sensitivity correction method for a dose monitoring device in Embodiment 4.
Figure 8:
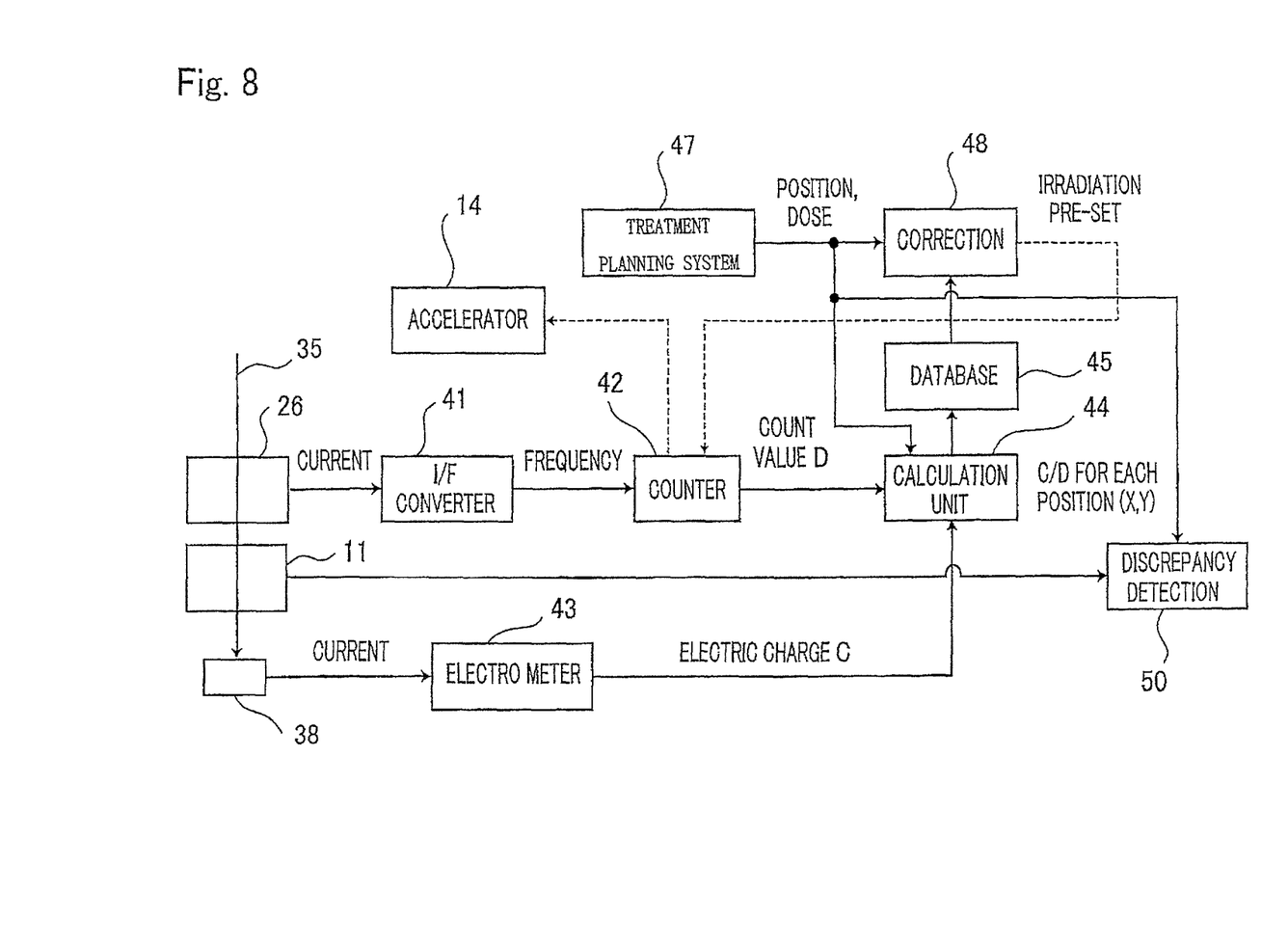
FIG. 8 is a block diagram showing a particle beam therapy system using a sensitivity correction method for a dose monitoring device in Embodiment 5.

Incidentally, block diagrams of the particle beam therapy system using the sensitivity correction method for the dose monitoring device according to Embodiment 1 are shown in FIG. 7 and FIG. 8.

Embodiment 2

In Embodiment 1, the irradiation position setting apparatus is provided, and on the basis of the irradiation position to be set based on the energy of the particle beam and the amount of excitation of the X,Y direction scanning electromagnets commanded by the irradiation position setting apparatus, the particle beam is scanned and the particle beam is irradiated to the irradiation position of the irradiation subject. However, in a similar way, a treatment planning system is provided, and on the basis of an irradiation position of an irradiation subject planned by the treatment planning system, a particle beam is scanned and the particle beam may be irradiated to the irradiation position of the irradiation subject. Incidentally, block diagrams of a particle beam therapy system using a sensitivity correction method for a dose monitoring device according to Embodiment 2 are shown in FIG. 7 and FIG. 8.

Furthermore, as for confirmation of the irradiation position of the irradiation subject, as described above, an irradiation position (x,y) on an XY flat surface of the irradiation position of the irradiation subject may be measured (measured and converted) and confirmed using a position monitor 11.

Embodiment 3

Figure 6:
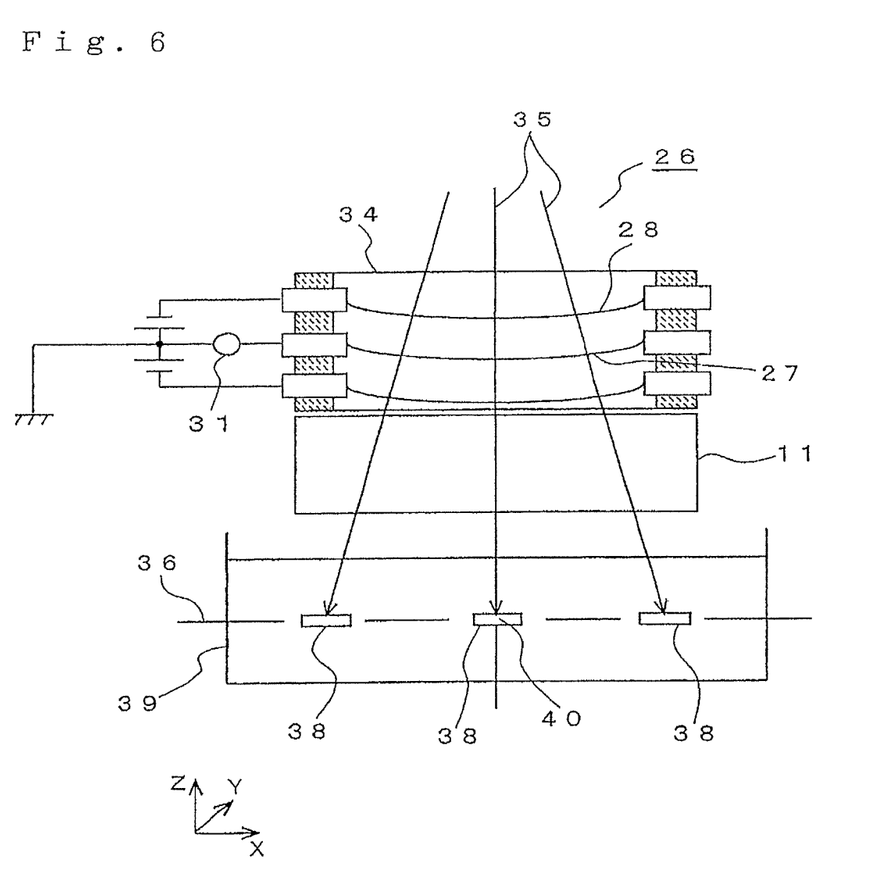
FIG. 6 is a view for explaining a sensitivity correction method for a dose monitoring device in Embodiment 3.

FIG. 6 is a view for explaining a sensitivity correction method for a dose monitoring device in Embodiment 3. A correction coefficient which corrects sensitivity of a dose monitoring device 26 is preferably found in a state near actual irradiation of a particle beam therapy system. In FIG. 6, as in Embodiment 1, a dose monitoring device 26, a position monitor 11, and a small parallel flat plate type ionization chamber 38 are provided. In Embodiment 3, a water phantom 39 is disposed at a position where an angle of a rotating gantry 19 (FIG. 1) is 0 degrees and an isocenter 40 is included; and the small parallel flat plate type ionization chamber 38 is disposed on an XY flat surface 36 which includes the isocenter 40 and is perpendicular to an axis (Z axis) of a traveling direction of a particle beam and the ionization chamber 38 is moved to an irradiation position. The correction coefficient of the dose monitoring device 26 can be found as in Embodiment 1, 2. If the correction coefficient of the dose monitoring device 26 has been found, the water phantom 39 and the small parallel flat plate type ionization chamber 38 are removed before actual irradiation of the particle beam therapy system. The correction coefficient of the dose monitoring device 26 can be found during adjustment of the particle beam therapy system and, further, the correction coefficient may be periodically found.

Embodiment 4

FIG. 7 is a block diagram showing a particle beam therapy system using a sensitivity correction method for a dose monitoring device in Embodiment 4. A dose monitoring device 26 measures a dose of an irradiated particle beam and obtains a current corresponding to the strength of the dose. The current is converted to frequency corresponding to the current by an I/F converter 41, the converted frequency is converted to a count value (D) corresponding to the frequency by a counter 42, and the converted count value (D) is introduced to a calculation unit 44. A position sensor 11 measures (converts and measures) an irradiation position (x,y) of an irradiation subject. The irradiation position (x,y) of the irradiation subject of the particle beam can be specified by the irradiation position planned by the treatment planning system described in Embodiment 2 and is introduced to the calculation unit 44. A small parallel flat plate type ionization chamber 38 measures the dose of the particle beam passing through the dose monitoring device 26 and obtains the current corresponding to the strength of the dose; and an electro meter 43 obtains electric charge (C) corresponding to the current and the electric charge (C) is introduced to the calculation unit 44. Incidentally, the irradiation position (x,y) of the irradiation subject of the particle beam may use the irradiation position (x,y) of the irradiation subject converted and measured by the position sensor 11.

During adjustment of the particle beam therapy system, the particle beam therapy system is started up and, first, a particle beam 35 is irradiated on an axis (Z axis) of a traveling direction. The particle beam 35 passes through the original point (x=0, y=0) on the XY flat surface of the dose monitoring device 26 and the original point (x=0, y=0) on the XY flat surface of the position monitor 11; and then, the particle beam 35 reaches the small parallel flat plate type ionization chamber 38 disposed at the original point (x=0, y=0) on a predetermined XY flat surface. At this time, as far as the dose monitoring device 26 is concerned, current corresponding to the strength of the particle beam is converted to frequency by the I/F converter and then counted by the counter 42; and accordingly, a count value Do,o corresponding to an irradiation position (0,0) of an irradiation subject is measured. (Incidentally, the I/F converter 41 and the counter 42 are ordinarily provided as a part of the dose monitoring device 26.) As far as the position monitor 11 is concerned, the irradiation position (0,0) on the XY flat surface serving as the irradiation position of the irradiation subject is measured. The irradiation position (0,0) of the irradiation subject of the particle beam can be specified by the irradiation position planned by the treatment planning system. As far as the small parallel flat plate type ionization chamber 38 is concerned, current corresponding to the strength of the particle beam is obtained from the electro meter 43 and the obtained current is converted to electric charge Co,o of the small parallel flat plate type ionization chamber 38 corresponding to the irradiation position (0,0) of the irradiation subject. Accordingly, the calculation unit 44 obtains a calibration coefficient of the dose monitoring device 26 corresponding to the irradiation position (0,0) of the irradiation subject of the particle beam as follows:

$$ao,o = Co,o/Do,o$$

Next, the irradiation position of the irradiation subject is changed, the irradiation position of the particle beam on the XY flat surface of the dose monitoring device 26 is changed, and the small parallel flat plate type ionization chamber 38 is also changed to a position where the particle beam is irradiated on the predetermined XY flat surface. In this case, in a similar way, the irradiation position of the irradiation subject is measured by the position monitor 11. The irradiation position (x,y) of the irradiation subject of the particle beam can be specified by the irradiation position planned by the treatment planning system. The count value Dx,y is obtained by the dose monitoring device 26 and electric charge Cx,y is obtained by the small parallel flat plate type ionization chamber 38. Accordingly, the calculation unit 44 obtains a calibration coefficient of the dose monitoring device 26 corresponding to the irradiation position (x,y) of the irradiation subject of the particle beam as follows:

$$ax,y = Cx,y/Dx,y$$

Furthermore, the irradiation position of the irradiation subject is changed to other position, the irradiation position of the particle beam on the XY flat surface of the dose monitoring device 26 is changed to other position, and the small parallel flat plate type ionization chamber 38 is also changed to other position where the particle beam is irradiated on the predetermined XY flat surface; and accordingly, a calibration coefficient ax,y of the dose monitoring device 26 corresponding to other irradiation position (x,y) of the irradiation subject of the particle beam can be obtained by the calculation unit 44 in a similar way.

Further, by the calculation unit 44, the calibration coefficient ao,o of the dose monitoring device 26 in which the irradiation position of the irradiation subject corresponds to the position (0,0) is set as a reference, and a correction coefficient Ax,y corresponding to other irradiation position (x,y) of the irradiation subject is found as a ratio of the calibration coefficient ao,o with respect to a reference position (0,0) as follows:

$$Ax,y = ax,y/ao,o$$

In this way, the correction coefficient Ax,y of the dose monitoring device 26 corresponding to for each irradiation position of the irradiation subject of the particle beam, the correction coefficient Ax,y being found by the calculation unit 44, is stored in a database 45.

On the other hand, plans for patients are made by a treatment planning system 47. In the plans, an irradiation position and a given dose of an irradiation subject of each spot is designated. Among the designation, as for the given dose for each irradiation position, a correction unit 48 performs sensitivity correction in accordance with the correction coefficient for each irradiation position of the database 45. In the case of actual treatment, a dose in which the sensitivity correction is performed for each irradiation position is sent as irradiation pre-set; and irradiation of the particle beam is performed based on the irradiation pre-set. An irradiation pre-set value and a value corresponding to the dose measured by the dose monitoring device 26 are compared by the counter 42; and when the value corresponding to the dose is the irradiation pre-set value, an accelerator 14 is controlled and treatment irradiation is completed.

Embodiment 5

FIG. 8 is a block diagram showing a particle beam therapy system using a sensitivity correction method for a dose monitoring device in Embodiment 5. In Embodiment 5, as in Embodiment 4, plans for patients are made by a treatment planning system 47. In the plans, an irradiation position and a given dose of an irradiation subject of each spot is designated. Among the designation, as for the given dose for each irradiation position, a correction unit 48 performs sensitivity correction in accordance with a correction coefficient for each irradiation position of a database 45. In the case of actual treatment, a dose in which the sensitivity correction is performed for each irradiation position is sent as irradiation pre-set; and irradiation of the particle beam is performed based on the irradiation pre-set. At this time, a position monitor 11 measures the irradiation position of the irradiation subject and inputs measured irradiation position (x,y) data to a discrepancy detector 50. On the other hand, irradiation position (x,y) data of the irradiation subject of each spot made by the treatment planning system 47 is inputted to the discrepancy detector 50. When the discrepancy between both inputs exceeds a predetermined set value, discrepancy information is sent. In this way, the discrepancy of the irradiation position of the particle beam may be detected.

Embodiment 6

Figure 9:
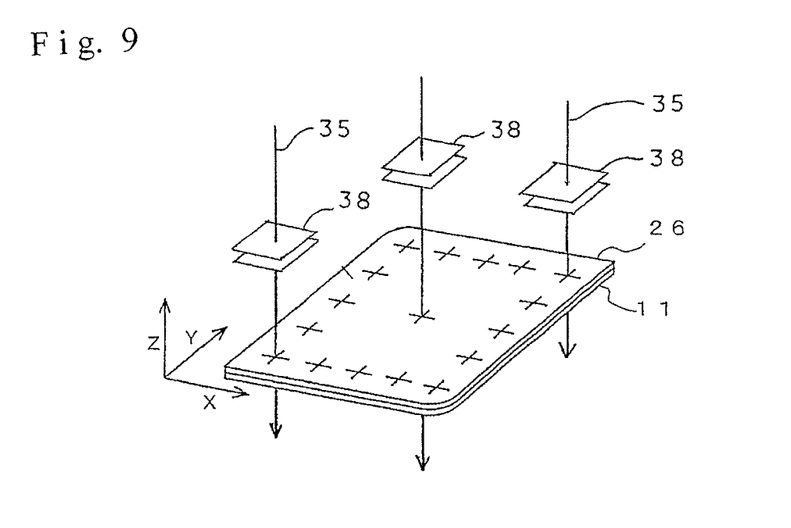
FIG. 9 is a view explaining a sensitivity correction method for a dose monitoring device in Embodiment 6.

In Embodiment 1, the description has been made on the case where the small parallel flat plate type ionization chamber is located in the lower stream of the dose monitoring device; however, the small parallel flat plate type ionization chamber may be located in an upper stream of the dose monitoring device, as depicted, for example, in FIG. 9. In this case, a dose of a particle beam 35 is measured by the small parallel flat plate type ionization chamber 38 in a state where a beam position before being scanned by scanning electromagnets is not fluctuated from a beam axis or in a state where, after being scanned, a fluctuation width before reaching the dose monitoring device 26 is smaller than a position of the dose monitoring device 26; and therefore, the small parallel flat plate type ionization chamber 38 can be naturally smaller than the dose monitoring device 26 and the ionization chamber 38 does not need to be moved according to the beam position on the XY flat surface perpendicular to the beam axis. Therefore, the small parallel flat plate type ionization chamber 38 can be used being fixed on the beam axis. In the case of Embodiment 6, the small parallel flat plate type ionization chamber 38 is not present at an irradiation position (isocenter) to a diseased part; and therefore, there is an advantage in that the small parallel flat plate type ionization chamber 38 does not disturb the irradiation and does not need to be removed from a particle beam line after sensitivity correction.

Various modifications and alternations of this invention can be achieved to those skilled in the art without departing from the scope and spirit of this invention, and it should be understood that this is not limited to the respective illustrative embodiments set forth in the description.

The invention claimed is:

1. A sensitivity correction method for a dose monitoring device included in a particle beam therapy system which scans a particle beam and irradiates the particle beam to an irradiation position of an irradiation subject, the sensitivity correction method comprising the steps of:
    measuring, by said dose monitoring device, the dose of the particle beam passing through said dose monitoring device;
    measuring, by a small ionization chamber that is smaller in size than said dose monitoring device, the dose of the particle beam that passes through said dose monitoring device, wherein said small ionization chamber is located downstream of said dose monitoring device with respect to the traveling direction of the particle beam; and
    calculating, by a calculation unit, a correction coefficient of the dose measured by said dose monitoring device corresponding to the irradiation position based on the dose of the particle beam measured by said small ionization chamber, for improving measurement deterioration due to deflection of an electrode of the dose monitoring device.

2. The sensitivity correction method for the dose monitoring device according to claim 1, wherein said particle beam therapy system further includes a treatment planning system, the method further comprising:
    scanning the particle beam and irradiating the particle beam to the irradiation position of the irradiation subject, on the basis of the irradiation position of the irradiation subject planned by said treatment planning system; and
    calculating, the correction coefficient of the dose measured by said dose monitoring device corresponding to the irradiation position.

3. The sensitivity correction method for the dose monitoring device according to claim 1, wherein said particle beam therapy system further includes a treatment planning system, the method further comprising:
    scanning the particle beam and irradiating the particle beam to the irradiation position of the irradiation subject, on a basis of the irradiation position to beset based on energy of the particle beam and the amount of excitation of X,Y direction scanning electromagnets commanded by said treatment planning system; and
    calculating the correction coefficient of the dose measured by said dose monitoring device corresponding to the irradiation position.

4. The sensitivity correction method for the dose monitoring device according to claim 1, wherein said particle beam therapy system further includes a position monitor of the particle beam, the method further comprising:
    measuring the irradiation position of the particle beam irradiated to said position monitor; and
    confirming the irradiation position of the irradiation subject of the particle beam.

5. The sensitivity correction method for the dose monitoring device according to claim 1,
    wherein said small ionization chamber is a parallel flat plate type.

6. The sensitivity correction method for the dose monitoring device according to claim 1, wherein
    the correction coefficient of said dose monitoring device in the case where the irradiation position of the irradiation subject of the particle beam is on an axis of a traveling direction of the particle beam is set as a standard, and
    the correction coefficient of the dose monitoring device in the case where the irradiation position of the irradiation subject of the particle beam is different from the axis is found by a ratio with the calibration coefficient is set as the standard.

7. The sensitivity correction method for the dose monitoring device according to claim 6,
    wherein said small ionization chamber includes an isocenter and is disposed on a flat surface perpendicular to the axis of the traveling direction of the particle beam.

8. A particle beam therapy system which scans a particle beam and irradiates the particle beam to an irradiation position of an irradiation subject, said particle beam therapy system comprising:
    a dose monitoring device which measures a dose of the particle beam;
    an ionization chamber that is smaller in size than said dose monitoring device, wherein said ionization chamber measures the dose of a particle beam passing through said dose monitoring device and is located downstream of said dose monitoring device with respect to the traveling direction of the particle beam; and
    a calculation unit which calculates a correction coefficient of the dose measured by said dose monitoring device corresponding to the irradiation position based on (i) the dose of the particle beam measured by said dose monitoring device, (ii) the irradiation position, and (iii) the dose of the particle beam passing through said dose monitoring device measured by said ionization chamber,
    wherein the irradiation dose is adjusted based on the correction coefficient, thereby improving measurement deterioration due to deflection of an electrode of the dose monitoring device.

9. The particle beam therapy system according to claim 8, further comprising a treatment planning system, wherein
    on a basis of the irradiation position of the irradiation subject planned by said treatment planning system, the particle beam is scanned and the particle beam is irradiated to the irradiation position of the irradiation subject; and
    the correction coefficient of the dose measured by said dose monitoring device corresponding to the irradiation position is found.

10. The particle beam therapy system according to claim 8, further comprising a treatment planning system, wherein
    on a basis of the irradiation position to be set based on energy of the particle beam and the amount of excitation of X,Y direction scanning electromagnets commanded by said treatment planning system, the particle beam is scanned and the particle beam is irradiated to the irradiation position of the irradiation subject; and
    the correction coefficient of the dose measured by said dose monitoring device corresponding to the irradiation position is calculated.

11. The particle beam therapy system according to claim 8, further comprising a position monitor of the particle beam, wherein
    the irradiation position of the particle beam irradiated to said position monitor is measured; and
    the irradiation position of the irradiation subject of the particle beam is confirmed.

12. The particle beam therapy system according to claim 8, wherein said ionization chamber is a parallel flat plate type.

13. The particle beam therapy system according to claim 8, wherein
    the correction coefficient of said dose monitoring device in the case where the irradiation position of the irradiation subject of the particle beam is on an axis of a traveling direction of the particle beam is set as a standard, and the correction coefficient of the dose monitoring device in the case where the irradiation position of the irradiation subject of the particle beam is different from the axis is found by a ratio with the calibration coefficient set as the standard.

14. The particle beam therapy system according to claim 13, wherein said ionization chamber includes an isocenter and is disposed on a flat surface perpendicular to the axis of the traveling direction of the particle beam.

15. The sensitivity correction method for the dose monitoring device according to claim 1, wherein said particle beam therapy system further includes a position monitor positioned proximate to said dose monitoring device, the method further comprises:

measuring the irradiation position of the particle beam irradiated to said position monitor.

16. The particle beam therapy system according to claim 8, further comprising a position monitor positioned in close proximity to said dose monitoring device, wherein said position monitor is configured to measure the irradiation position of the particle beam irradiated to said position monitor.

17. The sensitivity correction method for the dose monitoring device according to claim 1, further comprising:

converting the dose, measured by the dose monitoring device, to a count value corresponding to the irradiation position of the irradiation subject; and converting, by said small ionization chamber, the measured dose of the particle beam to electric charge corresponding to the irradiation position of the irradiation subject.

18. The particle beam therapy system according to claim 8, wherein the dose monitoring device is further configured to convert the dose, measured by the dose monitoring device, to a count value corresponding to the irradiation position of the irradiation subject; and the ionization chamber is further configured to convert the dose, measured by said ionization chamber, to electric charge corresponding to the irradiation position of the irradiation subject.

* * * * *